United States Patent [19]

Dulat et al.

[11] 4,067,990

[45] Jan. 10, 1978

[54] PROCESS FOR THE PREPARATION OF INSECTICIDAL COMPOSITIONS BASED ON CARBAMIC ESTERS

[75] Inventors: Marcel Louis Dulat, Poitiers; Claude Hennart, Seraincourt, both of France

[73] Assignee: Airwick Industries, Inc., Carlstadt, N.J.

[21] Appl. No.: 579,101

[22] Filed: May 20, 1975

Related U.S. Application Data

[63] Continuation-in-part of Ser. No. 298,158, Oct. 16, 1972, abandoned.

[30] Foreign Application Priority Data

Oct. 18, 1971 Luxembourg ............................ 64108

[51] Int. Cl.$^2$ .......................... A01N 9/20; A01N 9/28
[52] U.S. Cl. ..................................... 424/278; 424/282; 424/300
[58] Field of Search .......................................... 424/278

[56] References Cited

U.S. PATENT DOCUMENTS

| 3,111,539 | 11/1963 | Böcher et al. .................. 260/479 |
| 3,215,595 | 11/1965 | Böcher et al. .................. 424/300 |
| 3,238,091 | 3/1966 | Böcher et al. .................. 424/300 |
| 3,296,068 | 1/1967 | Addor ............................ 424/300 |
| 3,303,091 | 2/1967 | Mailander et al. ............. 424/45 |
| 3,470,236 | 9/1969 | Hausweiler et al. ........... 260/479 X |
| 3,641,060 | 2/1972 | Nakanishi et al. ............ 424/278 X |
| 3,644,633 | 2/1972 | Bachmann ..................... 424/278 |

FOREIGN PATENT DOCUMENTS

| 670,630 | 10/1965 | Belgium. |
| 115,020 | 1/1970 | Denmark. |
| 1,165,577 | 3/1964 | Germany. |
| 2,009,831 | 9/1970 | Germany. |
| 1,903,817 | 8/1970 | Germany. |
| 11,078 | 8/1956 | Germany. |
| 23,268 | 11/1967 | Japan. |
| 24,011 | 7/1971 | Japan. |
| 27,344 | 11/1968 | Japan. |
| 29,023 | 12/1968 | Japan. |
| 937,897 | 9/1963 | United Kingdom. |

OTHER PUBLICATIONS

The Condensed Chemical Dictionary, 6th Ed., p. 360.
Physico-Chemical & Biophysical Factors Affecting the Activity of Pesticides, pp. 18-23, (1968).

*Primary Examiner*—Allen J. Robinson
*Attorney, Agent, or Firm*—Harry Falber

[57] ABSTRACT

Insecticidal compositions in the form of a homogeneous liquid organic solution comprising as essential components:

A. from about 0.01 to 10% by weight, based on the weight of the composition of an insecticidal ortho-substituted phenyl N-methyl carbamate;

B. from about 0.01 to 10% by weight, based on the total weight of the composition of a liquid non-volatile to low-volatile organic diluent which has a weak solvent power for the active substance A and C. from about 25 to 99% by weight, based on the total weight of said composition of a liquid volatile organic solvent for the active substance A and D. from 0 to about 75% by weight, based on the total weight of said composition of a liquid moderately volatile to volatile organic diluent which has a weak solvent power for the active substance A.

7 Claims, No Drawings

PROCESS FOR THE PREPARATION OF INSECTICIDAL COMPOSITIONS BASED ON CARBAMIC ESTERS

The present invention is a continuation-in-part of the U.S. Pat. application Ser. No. 298,158 filed on Oct. 16, 1972, now abandoned.

The present invention relates to a process for the preparation of insecticidal compositions containing as insecticidally active component at least one compound pertaining to the class of phenyl N-methyl-carbamates, whereby the insecticidal action of the said compound is increased; the invention also relates to the compositions obtained by this process. The novel compositions can be either in the form of homogeneous liquid solutions containing, in addition to the mentioned carbamates, at least one organic liquid which is non volatile or slightly volatile and in which the said carbamates are difficultly soluble, and at least one other organic liquid which is highly volatile and in which the said carbamates are readily soluble; or they can be in the form of solid compositions prepared from these liquid solutions.

The use of N-methylcarbamic esters as insecticidal agents has been known for some years, and various types of compositions containing these agents have been recommended and/or marketed in the form of, for example, powders, baits in the form of granules or the like, and liquids.

Compositions in liquid form are widely used, since they can be applied in many different ways; liquids can be employed in all kinds of apparatus, and can be applied, for example, by means as varied as sprayers, brushes, and aerosol containers containing a compressed or liquefied gas; compositions in liquid form enable any desired degree of dilution to be obtained with an absolutely perfect dispersion of the active agent.

Liquid compositions can be prepared with solid carbamic esters in two main forms, namely as: suspensions and solutions.

Suspensions present problems well known to the users: their stability is always of short duration, so that in practice they can be prepared only at the moment of application, thus necessitating an additional operation when using them, and introducing for the manufacturer all the difficulties always associated with the production of wettable powders, such as the need for a very high degree of fineness and for the presence of at least two different surface-active agents chosen dependent on the active agent and on the fillers present in the powder. It is for these reasons that solutions are generally preferred. Nevertheless, these too have disadvantages: in particular, the presence of the liquids employed as solvents promotes penetration of the active agent into the porous materials on to which the solution is normally applied, such as walls and floors, for example. As a result, the efficacy of the composition applied on the surface of a treated material rapidly diminishes, a fact which is particularly undesirable where it is required obtain protection from harmful insects such as flies, mosquitoes, cockroaches, ants, wasps, etc.; this leads the user to repeat frequently the application of the composition, a practice which is uneconomical and which, moreover, results in the treated surfaces acquiring a soiled appearance in consequence of the accumulation of residual products.

It would be possible to use only highly volatile solvents, thus ensuring that the active agent crystallises on the surface of the treated material and can no longer be absorbed by it; however, the applicants has found that, the efficacy of the active agent is thereby greatly reduced.

The aforementioned drawbacks may also be overcome, at least in part by using solutions obtained with solvents which are only slightly volatile but in which the active agent is readily soluble, so that the resulting solutions have a high concentration of active agent; this, however, can be dangerous practice owing to the high toxicity of the N-methylcarbamic esters in these compositions.

Compositions which are homogeneous solutions of an active agent in a solvent of low volatility remain liquid for too long on the surface to which they have been applied, which renders them unusable in practice.

The present invention provides compositions free from all these drawbacks, which compositions were prepared based on the observation made by applicant that, when an ortho-substituted phenyl N-methyl-carbamate is first dissolved in a mixture of a liquid, slightly volatile diluent in which the said carbamate is difficultly soluble and of a volatile co-solvent which forms a homogeneous solution with the said carbamate and liquid, when the co-solvent is evaporated from the solution, the said carbamate is precipitated in a form which exhibits a greatly increased degree of insecticidal activity over a long period of time, even when the original homogeneous solution is applied on to the surface of an absorbent material.

The invention therefore provides a liquid insecticidal composition being in the form of a homogeneous solution and comprising:

A. an amount of ortho-substituted phenyl N-methyl-carbamate in an insecticidally effective amount but no more than can be completely dissolved in the remainder of the composition;

B. from 0.2 to 10 parts by weight, per part of active agent A, of at least one organic compound which is liquid at 25° C, slightly volatile, has a vapour pressure at 25° C not exceeding 0.01 Torr, and is able to dissolve, maximally 0.5 parts of active agent A in every 10 parts by weight of B at 20° C;

C. at least one organic compound which is liquid at 25° C, volatile in that is has a vapour pressure at 25° C, volatile in that it has a vapour pressure at 25° C of at least 5 Torr, and being able to dissolve at 20° C at least 5% by weight of compound A this organic compound C being present in an amount sufficient to form a complete and homogeneous solution with components A and B present in the composition.

The liquid insecticidal composition according to the invention can optionally contain one or more adjuvants which are soluble in the mixture formed by A + B + C and are selected from:

D. the class of diluents being able to dissolve only less than 5% by weight of compound A, and being liquids having a vapour pressure above 0.01 Torr at 25° C;

E. liquefied gases usable as propellants;

F. complementary insecticidally active agents the physical properties of which are different from those of components B, C and D described above;

G. dyestuffs,

H. perfumes and

I. inert solid diluents or fillers.

The ortho-substituted phenyl N-methyl-carbamate present in the compositions according to the invention corresponds preferably to the following formula:

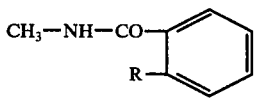

(I)

wherein R is an alkyl radical containing one to five carbon atoms, or an alkoxy radical containing one to four carbon atoms, or a propargyloxy radical, or a diethoxymethyl radical, or a dimethoxymethyl radical or a 1,3-dioxan-2-yl or 1,3-dioxolan-2-yl radical, which latter two radicals are unsubstituted or substituted by one or two methyl groups.

Examples of such carbamates are:
orthocresyl N-methyl-carbamate,
2-ethyl-phenyl N-methyl-carbamate,
2-isopropyl-phenyl N-methyl-carbamate,
2-tertiobutyl-phenyl N-methyl-carbamate,
2-sec-butyl-phenyl N-methyl-carbamate,
2-tertioamyl-phenyl N-methyl-carbamate,
2-methoxy-phenyl N-methyl-carbamate,
2-ethoxy-phenyl N-methyl-carbamate,
2-isopropoxy-phenyl N-methyl-carbamate,
2-isobutoxy-phenyl N-methyl-carbamate,
2-tertiobutoxy-phenyl N-methyl-carbamate,
2-sec-butoxy-phenyl N-methyl-carbamate,
2-propargyl-phenyl N-methyl-carbamate,
2-dimethoxy-methyl-phenyl N-methyl-carbamate,
2-diethoxy-methyl-phenyl N-methyl-carbamate,
2-(1,3-dioxolan-2-yl)-phenyl N-methyl-carbamate,
2-(4-methyl-1,3-dioxolan-2-yl)-phenyl N-methyl-carbamate,
2-(4,5-dimethyl-1,3-dioxolan-2-yl)-2-phenyl N-methyl-carbamate,
2-(1,3-dioxan-2-yl)-phenyl N-methyl-carbamate,
2-(4-methyl-1,3-dioxan-2-yl)-phenyl N-methyl-carbamate.

Of the preceding compounds, 2-(1,3-dioxolan-2-yl)-phenyl N-methyl-carbamate or Dioxacarb having the following formula:

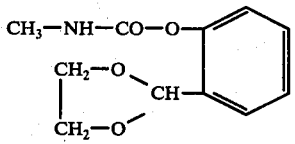

(II)

and described in Belgian Pat. No. 670,630 and 2-isopropoxyphenyl N-methyl-carbamate or Arprocarb of the following formula:

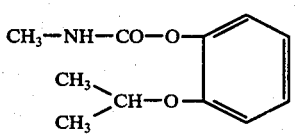

(III)

are preferred.

Preferably, the amount of component A does not exceed 10% of the total weight of the liquid composition, and constitutes at least 0.2% of the total weight of the components A + B + C.

The liquid organic components B, C and D can from instance be selected from one or several members of the following chemical classes: aliphatic hydrocarbons, halogenated aliphatic hydrocarbons, aromatic hydrocarbons, halogenated aromatic hydrocarbons, aliphatic and aromatic esters, oxygenated heterocyclic compounds, aliphatic mono- and polyalcohols, aminoalcohols, ethers, ether-alcohols, aliphatic mercaptans, ketones, aliphatic acids and anhydrides, nitro-alkanes, nitriloalcanes and natural oils.

The low-volatile liquid diluent B is used in a proportion of between 0.2 and 10 parts by weight to one part of active substance A; preferably, diluent B is employed in proportions of between 0.01 and 10% of the weight of the final liquid composition. It has been observed, in fact, that below 0.2 part by weight the effect produced by the low-volatile diluent B becomes too small to be of use; above 10 parts by weight the effect is indeed still maintained, but the compositions, after application, remains too liquid, and the previously mentioned disadvantages are again experienced, which is an indication that compositions remain, after their application, in a state of homogeneous solution. The most preferred proportions are between 1 and 5 parts by weight of low-volatile diluent B one part by weight of active substance.

The low-volatile liquid diluent B preferably has a vapour pressure at 25° C below 0.005 Torr. It can be completely non-volatile and have a vapour pressure which is inferior to $10^{-6}$ Torr. Its maximum dissolving capacity for the active substance A at 20° C is 5 parts by weight of A to 100 parts by weight of B; the preferred maximum proportion of A is 3 parts by weight. Consequently, the total amount of active substance A present in the composition and dissolved in liquid B, after evaporation of liquid C, cannot exceed 50% of the weight of A, and in the case of the preferred limits, the maximum amount dissolved in B is 15% of the weight of A. This constitutes a main feature of the invention.

The low volatile diluent B can for instance be selected from one or several of the following chemical groups:
aliphatic hydrocarbons having from 4 to 24 carbon atoms, halogenated aliphatic hydrocarbons having from 14 to 18 carbon atoms,
halogenated aromatic hydrocarbons,
aliphatic esters having a total of from 14 to 22 hydrocarbons,
aromatic esters,
oxygenated heterocyclic compounds,
aliphatic monoalcohols having 12 or 13 carbon atoms, aliphatic polyols, ethers and ether-alcohols,
aliphatic mercaptans of from 10 to 14 carbon atoms,
saturated and unsaturated aliphatic ketones having from about 14 to 18 carbon atoms,
aliphatic saturated and unsaturated acids of from about 14 to 18 carbon atoms and anhydrides thereof,
natural oils.

Examples of liquid diluents B which can be used in the compositions according to the present invention are:

| Compound B | Dissolution capacity at 20° C in weight-% for DIOXACARB | ARPROCARB | Vapour pressure in Torr at 25° C |
| --- | --- | --- | --- |
| Vaselin oil (y) | 0 | 0 | <0.0001 |
| Parafin oil | 0 | 0 | <0.0001 |
| Hexadecane | 0 | | 0.003 |
| 1-Chlorohexadecane | 0.7 | 0.4 | <0.0001 |
| 1-Bromotetradecane | 0.1 | | <0.001 |
| Tetrachlorodiphenyle | 1.3 | | <0.001 |
| Isopropylmyristate | 0.3 | 1.3 | ≈0.001 |
| Di(2-ethylhexyl)adipate) | 2.0 | 2.8 | 0.007 |
| Dibutylphthalate | 2.7 | | <0.0001 |
| Dioctylphthalate | 0.1 | 2.6 | <0.0001 |
| T.U.O.B. (a) | 2.9 | 5.0 | <0.005 |
| 1-Dodecanol | 0.8 | | 0.001 |
| Glycerol | 0.6 | | <0.0001 |
| 5,8,11-Trioxapentadecane | 3.2 | | 0.002 |
| 2-Amino-2-ethyl-1,3-propanediol | 2.4 | | 0.01 |
| ter. Dodecanethiol | 0.2 | | 0.008 |
| Oleone | 0.2 | | <$10^{-6}$ |
| Octanoic acid | 1.5 | | 0.002 |
| Oleic acid | 1.2 | | 0.0002 |
| 2-Dodecylsuccinic-acid anhydride | 2.9 | | 0.007 |
| Olive oil | 0.4 | | <0.0001 |
| Line oil | 0.5 | | <0.0001 |

(a) abbreviation for 5-(3,6,9-trioxa-undecyl-2-oxy)-1,3-benzodioxole.
(y) semi-refined vaseline oil having a density of 0.87 at 15° C and a viscosity of 1.7° Engler at 50° C.

Among these von-volatile to low-volatile diluents B, vaseline oil, paraffin oil, hexadecane, 1-chlorohexadecane, 1-bromotetradecane, tetrachlorodiphenyl, isopropylmyristate, di(ethyl-2-hexyl) adipate, dibutylphthalate, dioctylphthalate and 5-(3,6,9-trioxa-undecyl-2-oxy)-1,3-benzodioxole, because of their very low volatility (their vapour pressure at 25° C is inferior to 0.005 Torr) and their high to total miscibility with a great number of solvents C and diluents D, are particularly preferred.

The volatile liquid solvent C has a vapour tension at 25° C at least equal to 5 Torr, and preferably a vapour tension at 25° C of above 80 Torr but this vapour pressure can be as high as 600 Torr. But most preferably, the vapour pressure at 25° C of the volatile solvent C lies within the range of about 150 to 450 Torr. It is preferably miscible in any proportion with diluent B; its dissolving capacity with respect to active substance A, at 20° C, is at least 5% by weight, and preferably above 20%; most preferably the solvent C is able to dissolve from about 25 to 50% by weight of component A. The amount of solvent C required in the composition depends, as already mentioned, on its capacity to dissolve the active substance A, on its miscibility with the diluent B and on the amount of each of these components; and it must always suffice to obtain a complete and homogeneous solution; preferably, the proportion employed of solvent C is between 25 and 90% of the total weight of the components A + B + C.

The volatile solvent C is preferably selected from the following chemical classes:

halogenated methane, aliphatic mono- and diesters having a total of from 3 to 6 carbon atoms, monocyclic oxygenated heterocyclic compounds, aliphatic alcohols and ether-alcohols having from 1 to 3 carbon atoms, aliphatic ketones with 2 to 3 carbon atoms and other light solvents such as nitroalcanes and nitriloalkanes with 1 to 3 carbon atoms.

Examples of such volatile solvents which can be used in the compositions according to the invention are:

| Compound C | Dissolution capacity at 20° C in weight % for DIOXACARB | ARPROCARB | Vapour pressure in Torr at 25° C |
| --- | --- | --- | --- |
| Dichloromethane | 45 | 48 | 420 |
| Trichloromethane | 34 | | 194 |
| Methylacetate | 19.6 | 41 | 216 |
| Ethylacetate | 10.5 | | 97 |
| Propylacetate | 6 | | 33 |
| Isopropylacetate | 6 | | 55 |
| Butylacetate | 5 | | 11 |
| Isobutylacetate | 6 | | 17 |
| sec. Butylacetate | 6 | | 26 |
| Methylpropionate | 12 | | 83 |
| Ethylpropionate | 9 | | 37 |
| Methylbutyrate | 8 | | 34 |
| Ethylbutyrate | 7 | | 17 |
| 2-Methoxyethyl acetate | 20 | 33 | 5 |
| Tetrahydrofuran | 33.5 | 50 | 176 |
| Dioxan | 23 | | 35 |
| 2-Methoxyethanol | 15 | | 8.6 |
| Methanol | 20.5 | | 127 |
| Ethanol | 0.2 | 0.3 | 151 |
| Isopropanol | | 30 | 44 |
| Acetone | 28 | | 225 |
| Methylethylketone | 5 | | 20 |
| Nitromethane | 27.5 | | 34 |
| Acetonitrile | 35.5 | | 86 |

Because of their high volatility (vapour pressure at 25° C ranging from about 150 to 450 Torr) and their complete miscibility with most of the diluents, dichloromethane, trichloromethane, tetrahydrofuran, acetone and mixtures thereof are particularly appreciated solvents C. Mixtures of tetrahydrofuran and of dichloromethane in weight proportions of about 1:10 are equally much appreciated.

Volatile liquid diluents D are selected from among the organic liquids inert to the other constituents of the composition; they should have a vapour pressure of between 0.01 to 10 Torr, and be capable of dissolving not more than 5% of active substance A at 20° C. When using them, the necessary proportion of diluent B can be reduced and, as these volatile diluent evaporate appreciably more rapidly than the non-volatile diluent B, they impart after a certain time, a drier appearance to the residual composition after application and evaporation of the solvent C; liquid volatile diluents D having a vapour pressure of above 10 Torr and as high as of about 100 Torr may also be used, especially in order to dilute the solvent C when the latter possesses a very high dissolving capacity for A. The volatile diluents D preferably show for the active substance A a dissolving capacity of from about 0.005 to 0.5% by weight of component A. Liquid volatile diluents D are generally employed in proportions of at most 75% of the total weight of the liquid composition. Suitable as liquid volatile diluents D are for example, liquid saturated hydrocarbons, liquid aromatic hydrocarbons, liquid dialkyl ethers, liquid aliphatic saturated alcohols having at least three carbon atoms, and liquid chloroalkanes.

The volatile diluent D is preferably selected from:

light fraction of petroleum having a distillation range between 70 and about 250° C such as aliphatic hydrocarbons containing 5 to 18 carbon atoms, halogeno alkanes having 2 to 4 carbon atoms, aromatic hydrocarbons and alcohols of from 3 to 5 carbon atoms.

The following organic diluents are particularly suitable as component D in the compositions according to the invention:

| Compound D | Dissolution capacity at 20° C in weight % for | | Vapour pressure at 25° C in Torr |
|---|---|---|---|
| | DIOXACARB | ARPROCARB | |
| Pentane | 0.2 | 0.3 | 513 |
| Hexane | 0.2 | 0.3 | 151 |
| Heptane | | 0.3 | 38.5 |
| Ligroin (b) | <0.1 | 0.2 | 80 |
| Isopar L (b') | <0.1 | | 0.2-2 |
| Isopar G (x') | <0.1 | | 15-20 |
| 1-Chlorobutane | 2 | | 102 |
| 1.1.1-Trichloroethane | 2.3 | | 121 |
| Trichloroethylene | 2 | | 74 |
| Benzene | 3 | | 95 |
| Isopropanol | 4.5 | | 44 |
| Amylalcohol | 2.6 | | 2.5 |

Among the above-listed volatile diluents D the hydrocarbons having a vapour pressure at 25° C from 0.2 to 100 Torr such as Ligroin, Isopar L and Isopar G are particularly preferred. Isopropanol is also much appreciated as component D when DIOXACARB is used in the composition.

The weight proportions of components A, B and C present in the composition preferably lie within the following ranges: from about 1 to 2 parts by weight of active substance A, about 1 to 2 parts by weight of diluent B and about 10 to 10,000 parts by weight of solvent C.

The liquefied gases E employed as propellants are selected, for example, from the following: butane, isobutane, propane, dimethyl ether, trichlorofluoromethane, dichlorodifluoromethane, 1,2-dichloro-1,1,2,2-tetrafluoroethane, tetrafluoromethane and octafluorocyclobutane. The complementary insecticidal agents F are preferably substances in which the active substance A is not soluble or only slightly soluble. They are chosen, for example, from the following: phosphoric esters, phosphonic esters, thiophosphoric esters, natural pyrethrins, rotenone, synthetic pyrethrinoids, N,N-dibutyl-parachlorobenzene-sulphonamide, 1,4,4a,5,6,7,8,8-octahydro-3a,4,7,7a-tetrahydro-4,7-methano-indene, hexachlorocyclohexane, endoexo-1,2,3,4,10,10-hexachloro-6,7-epoxy-1,4,4a,5,6,7,8,8a-octahydro-1,4,5,8-dimethane-naphthalene and carbamic esters different from A, e.g. 1-dimethylcarbamyl-5-methyl-pyrazol-3-yl, 3-methyl-1-phenyl-5-pyrazolyl-dimethyl-carbamate and 4-methyl-2-propyl-6-pyrimidyl dimethyl-carbamate.

Generally, liquids which have, at the same time, a very low volatility and a high dissolving capacity for the active agent A should not be added to the compositions according to the invention. It is also preferable to avoid a content of water in excess of the amount corresponding to the normal water content of commercial chemical products.

Inert solid diluents I are preferably chosen from among the natural or synthetic waxy substances, the natural or synthetic hard resins and the solid non-waxy hydrocarbons; they are used preferably in small proportions not exceeding 10% by weight of the composition, and render possible the obtainment of insecticidal lacquers, floor-polishes and varnishes, after evaporation of the volatile liquids.

Diluents of waxy consistency are selected, for example, from the following: beeswax, candelilla wax, carnauba wax, Japan wax, montan wax, synthetic chloronaphthalene waxes, glycol stearates and solid fatty ketones.

Hard resin diluents are selected, for example, from the following: colophonium, shellac, cellulose derivatives (methyl ether, ethyl ether, benzyl ether, acetate, propionate, butyrate, phthalate, nitrate, etc.), and synthetic organic resins such as the homopolymers and copolymers obtained from vinyl derivatives (acetate, propionate, butyrate, oxides, formaldehyde, acetal, butyral, chloride, etc.) and/or from vinylidene derivatives, and/or from alkenes (ethylene, propylene, butylene, etc.), and/or from styrene, and/or from vinylpyrrolidones, and/or from acrylic or methacrylic esters (methyl, ethyl, propyl, butyl esters), and/or from allyl esters (phthalate, isophthalate, maleate, cyanurate, etc.). Such synthetic organic resins can be obtained also from the reaction of compounds having reactive groupings, such as is the case with regard to the resins known as "epoxy" resins, resulting from the condensation of an epoxide with a polyphenol, the "polyester" resins resulting from the action of a polyacid on a polyol, the polyurethanes resulting from the condensation of a polyisocyanate with a polyol, and the resins of the coumarone-indene type.

Solid hydrocarbon diluents are selected, for example, from among the microcrystalline and macrocrystalline alkanes having at least 24 carbon atoms, and mixtures thereof known under the name of microwax, tank bottom wax, ozokerite, ceresin, paraffin and isoparaffin.

The liquid compositions according to the invention are destined for application to any surface frequented by the insects to be destroyed; the said compositions can also be used for the preparation of solid products are prepared by the impregnation of carriers with the liquid composition according to the invention, the said carriers being, for example, cellulose board, asbestoss board, waste-paper, wool and/or cotton felt, mineral or organic granules and powders, such as talcum, kaolin, dried clay, fossil silica, synthetic silica, non-fossil natural silica, vermiculite, magnesium silicate, aluminium silicate, calcium phosphate, calcium carbonate, soya bean flour, nutshell flour.

After impregnation of the solid carrier, the liquid solvent C and if present the volatile liquid diluent D, are evaporated off by a method known per se, e.g. a current of air or hot inert gas, in order to obtain the final solid product.

The invention, therefore, also provides a process for the preparation of a solid insecticidal composition containing the components A and B and, optionally, low-volatile or non-volatile D, E, F, G or H, already defined, the said process comprising the application of the previously described liquid composition still containing the component C on to a solid surface, the solvent C being then evaporated or allowed to evaporate off. The solid surface may be that of a solid carrier selected from materials such as cardboard, felt, or mineral or organic granules and powders. The said support is, for example, impregnated with a composition according to the invention, containing the components A, B and C and, optionally, D, E, F, G or H, and the liquid C is then evaporated.

The usefulness of the compositions according to the invention is illustrated by the tests described in the following.

|  | Component | A-0 | A-1 | A-2 |
|---|---|---|---|---|
| Dioxacarb | A | 2 | 2 | 2 |
| T.U.O.B. (a) | B | — | 4 | — |
| Dibutyl phthalate (a') | B | — | — | 4 |
| Dichloromethane (b') | C | 27 | 25 | 25 |
| Ligroin (b) | D | 16 | 14 | 14 |
| Trichlorofluoromethane | E | 22 | 22 | 22 |
| Dichlorodifluoromethane | E | 33 | 33 | 33 |

(a) abbreviation for 5-(3,6,9-trioxa-undecyl-2-oxy)-1,3-benzodioxole: liquid possessing a vapour pressure at 25° C of below 0.005 Torr, and at 20° C a dissolving capacity of 2.9% with respect to Dioxacarb; and of 5% with respect to Arprocarb;
(a') liquid having a vapour pressure at 25° C of ca. 0.0001 Torr, and a dissolving capacity of 2.7% with respect to Dioxacarb, at 20° C;
(b) distillation range of between 92 and 101° C, obtained from a petroleum of North American origin, possessing a vapour pressure at 25° C of ca. 80 Torr, and a dissolving capacity of below 0.1% with respect to Dioxacarb, at 20° C;
(b') liquid having a vapour pressure at 25° C of 420 Torr, and a dissolving capacity of 45% with respect to Dioxacarb, at 20° C.

The contents of these containers was sprayed each on to one of the two faces of wooden plates (Okoume plywood), 20 × 10 cm in size, in an amount of 500 mg per plate; five such plates were prepared for each composition. These plates were maintained at 30° C for 12 days, and tests to determine the insecticidal efficacy of the respective compositions were carried out periodically with common cockroaches (Blatta orientalis) as the test insects; these were placed on to the treated faces of the plates for one minute, and then placed for observation in ventilated glass jars; a count of the cumulative proportion of dead insects or insects in dorsal position was taken and recorded every 30 minutes; the number of insects used for each composition was about 50. The recorded results are given in the table below.

| COMPOSITION | AGE (days) | TIME IN MINUTES | | | |
|---|---|---|---|---|---|
| | | 30 | 60 | 90 | 120 |
| A-0 | 1 | 0 | 7 | 25 | 67 |
| A-1 | | 2 | 15 | 57 | 87 |
| A-2 | | 0 | 52 | 80 | 95 |
| A-0 | 2 | 2 | 20 | 67 | 77 |
| A-1 | | 12 | 32 | 75 | 87 |
| A-2 | | 7 | 57 | 85 | 100 |
| A-0 | 5 | 0 | 13 | 26 | 36 |
| A-1 | | 2 | 32 | 60 | 80 |
| A-2 | | 0 | 17 | 42 | 65 |
| A-0 | 7 | 3 | 3 | 40 | 47 |
| A-1 | | 5 | 22 | 67 | 80 |
| A-2 | | 12 | 45 | 87 | 100 |
| A-0 | 12 | 0 | 22 | 70 | 92 |
| A-1 | | 7 | 35 | 100 | — |
| A-2 | | 0 | 67 | 100 | — |

TEST A'

The plates prepared using the composition A-0 and A-2 as defined in Test A were tested under the conditions described in said test, the test insects in the present case being German cockroaches (Blattella Germanica); the following results were recorded up to the 40th day.

| COMPOSITION | AGE (days) | TIME IN MINUTES | | | |
|---|---|---|---|---|---|
| | | 30 | 60 | 90 | 120 |
| A-0 | 1 | 35 | 57 | 67 | 70 |
| A-2 | | 65 | 90 | 95 | 100 |
| A-0 | 2 | 32 | 67 | 85 | 100 |
| A-2 | | 47 | 87 | 100 | — |
| A-0 | 7 | 10 | 10 | 37 | 57 |
| A-2 | | 12 | 67 | 100 | — |
| A-0 | 12 | 5 | 15 | 20 | 27 |
| A-2 | | 10 | 42 | 80 | 87 |
| A-0 | 40 | 37 | 60 | 82 | 100 |
| A-2 | | 52 | 90 | 100 | — |

TEST B

The following three compositions B-0, B-1 and B-2 were prepared and filled in aerosol containers (values expressed in percent by weight):

| Component | | B-0 | B-1 | B-2 |
|---|---|---|---|---|
| A | Dioxacarb | 2 | 2 | 2 |
| B | T.U.O.B. (a) | — | 2 | 4 |
| C | Dichloromethane (b') | 32 | 32 | 32 |
| E | Trichlorofluoromethane | 25 | 25 | 25 |
| E | Dichlorodifluoromethane | 25 | 25 | 25 |
| D | "Isopar L" (b") | 16 | 14 | 12 |

(b") distillation range between 189 and 205° C of branched aliphatic hydrocarbons obtained by synthesis, marketed by the firm Esso Standard, containing a mixture of decane, undecane and dodecane, possessing at 25° C vapour pressures of between 0.2 and 2 Torr, and having a dissolving capacity at 20° C below 0.1% with respect to Dioxacarb.

The content of each of these containers was distributed, by spraying, over one of the faces of a glass plate, 20 × 10 cm in size, the amount applied being 600 mg per plate.

These plates were maintained at 20° C for 30 days, and the insecticidal action tests carried out on common cockroaches as described in Test A. The obtained results are given in the following table. It is seen, in particular, that, although the aliphatic hydrocarbon has a very low dissolving capacity for the active substance and relatively low volatility, its distillation range is not sufficient to impart to the composition B-0 a high degree of effectiveness, and that it is necessary to employ a liquid still less volatile, such as is defined under B in the present invention to obtain the desired result:

| COMPOSITION | AGE (days) | TIME IN MINUTES | |
|---|---|---|---|
| | | 30 | 60 |
| B-0 | 1 | 26 | 75 |
| B-1 | | 61 | 97 |
| B-2 | | 65 | 92 |
| B-0 | 2 | 5 | 52 |
| B-1 | | 40 | 69 |
| B-2 | | 72 | 95 |
| B-0 | 4 | 17 | 62 |
| B-1 | | 25 | 64 |
| B-2 | | 34 | 90 |
| B-0 | 7 | 5 | 30 |
| B-1 | | 13 | 75 |
| B-2 | | 17 | 75 |
| B-0 | 10 | 5 | 23 |
| B-1 | | 23 | 79 |
| B-2 | | 27 | 95 |
| B-0 | 15 | 10 | 57 |
| B-1 | | 20 | 75 |

-continued

| COMPOSITION | AGE (days) | TIME IN MINUTES 30 | 60 |
|---|---|---|---|
| B-2 | | 42 | 100 |
| B-0 | | 2 | 50 |
| B-1 | 21 | 30 | 67 |
| B-2 | | 30 | 85 |
| B-0 | | 10 | 52 |
| B-1 | 30 | 45 | 67 |
| B-2 | | 52 | 80 |

Tests A and A' are showing that the compositions according to the invention show satisfactory increased insecticidal activity against the two principal different cockroach families.

TEST C

The following three compositions, C-0, C-1 and C-2 were prepared and filled in aerosol containers (values expressed in percent by weight):

| Components | | C-0 | C-1 | C-2 |
|---|---|---|---|---|
| A | Dioxacarb | 3 | 3 | 3 |
| B | T.U.O.B. (a) | — | 3 | 6 |
| C | Dichloromethane (b') | 34 | 34 | 31 |
| E | Trichlorofluoromethane | 25 | 25 | 25 |
| E | Dichlorodifluoromethane | 25 | 25 | 25 |
| D | "Isopar L" (b") | 13 | 10 | 10 |

These compositions were tested as described in Test B and the obtained results are listed in the following table:

| COMPOSITION | AGE (days) | TIME IN MINUTES 30 | 60 |
|---|---|---|---|
| C-0 | | 44 | 72 |
| C-1 | 1 | 63 | 97 |
| C-2 | | 76 | 100 |
| C-0 | | 20 | 62 |
| C-1 | 2 | 76 | 98 |
| C-2 | | 89 | 100 |
| C-0 | | 16 | 65 |
| C-1 | 4 | 54 | 92 |
| C-2 | | 91 | 100 |
| C-0 | | 5 | 35 |
| C-1 | 7 | 26 | 92 |
| C-2 | | 66 | 100 |
| C-0 | | 15 | 57 |
| C-1 | 10 | 28 | 85 |
| C-2 | | 45 | 92 |
| C-0 | | 12 | 50 |
| C-1 | 15 | 44 | 100 |
| c-2 | | 92 | 97 |
| C-0 | | 10 | 37 |
| C-1 | 21 | 40 | 95 |

-continued

| COMPOSITION | AGE (days) | TIME IN MINUTES 30 | 60 |
|---|---|---|---|
| C-2 | | 42 | 100 |
| C-0 | | 5 | 45 |
| C-1 | 30 | 45 | 77 |
| C-2 | | 80 | 100 |

TEST C'

The compositions described in Test C were used for the preparation of steel plates having the dimensions of 20 × 10 cm, these samples being treated in the same manner as the glass plates in the said test. The tests were carried out with application of the same procedure and gave the following results:

| COMPOSITION | AGE (days) | TIME IN MINUTES 30 | 60 |
|---|---|---|---|
| C-0 | | 48 | 88 |
| C-1 | 2 | 65 | 100 |
| C-2 | | 72 | 100 |
| C-0 | | 12 | 77 |
| C-1 | 7 | 44 | 85 |
| C-2 | | 69 | 97 |
| C-0 | | 45 | 75 |
| C-1 | 21 | 65 | 97 |
| C-2 | | 60 | 97 |

Tests C and C' are showing that the insecticidal activity of the compositions according to the invention does not depend on the support on which said composition is applied.

TEST D

The following compositions D-0 to D-5 were prepared and filled in aerosol containers (values expressed in percent by weight):

| | Component | D-0 | D-1 | D-2 | D-3 | D-4 | D-5 |
|---|---|---|---|---|---|---|---|
| Dioxacarb | A | 2 | 2 | 2 | 2 | 2 | 2 |
| Dibutyl phthalate (a') | B | — | 4 | — | — | — | — |
| Isopropyl myristate (c) | B | — | — | 4 | — | — | — |
| Dioctyl phthalate (c') | B | — | — | — | 4 | — | — |
| Chlorohexadecane (c") | B | — | — | — | — | 4 | — |
| Tetrachlorodiphenyl (c''') | B | — | — | — | — | — | 4 |
| Tetrahydrofuran (d) | C | 2.5 | 2.5 | 2.5 | 2.5 | 2.5 | 2,5 |
| Dichloromethane (b') | C | 29.5 | 25.5 | 25.5 | 25.5 | 25.5 | 25.5 |
| Ligroin (b) | D | 11 | 11 | 11 | 11 | 11 | 11 |
| Trichlorofluoromethane | E | 22 | 22 | 22 | 22 | 22 | 22 |
| Dichlorodifluoromethane | E | 33 | 33 | 33 | 33 | 33 | 33 |

(c) liquid having at 25° C a vapour pressure of ca. 0.001 Torr and a dissolving capacity for Dioxacarb of 0.3%;
(c') liquid having at 25° C a vapour pressure of below 0.0001 Torr and a dissolving capacity for Dioxacarb of 0.1% at 20° C;
(c") liquid having at 25° C a vapour pressure of below 0.0001 Torr and a dissolving capacity for Dioxacarb of 0.7% at 20° C;
(c''') liquid containing a mixture of several tetrachlorodiphenyl isomers, having a vapour pressure at 25° C of below 0.001 Torr and a dissolving capacity for Dioxacarb of 1.3% at 20° C.
(d) liquid possessing a vapour pressure at 25° C equal to 176 Torr and a dissolving capacity for Dioxacarb of 33.5% at 20° C.

The contents of each of the containers was distributed, by spraying, over one of the two faces of glass plates each 20 × 10 cm in size, the applied amount being 600 mg per plate. After a standing time of 24 hours, tests for insecticidal efficacy were carried out on common cockroaches; these were placed on the treated face of the glass plates for a period of 30 seconds, and then transferred to ventilated glass jars for observation. The cumulative proportion of insects dead or in dorsal position was recorded every 3 minutes, the number of insects used being about 30 for each composition. The obtained results are given in the following table.

| TIME IN MINUTES | D-0 | D-1 | D-2 | D-3 | D-4 | D-5 |
|---|---|---|---|---|---|---|
| 6 | 0 | 10 | 0 | 0 | 3 | 0 |
| 9 | 0 | 30 | 0 | 0 | 13 | 0 |
| 12 | 0 | 87 | 20 | 40 | 27 | 3 |
| 15 | 3 | 100 | 77 | 70 | 43 | 20 |
| 18 | 3 | | 100 | 97 | 73 | 50 |
| 21 | 10 | | | 100 | 83 | 67 |
| 24 | 10 | | | | 93 | 97 |
| 27 | 10 | | | | 100 | 97 |
| 30 | 10 | | | | | 100 |
| 33 | 33 | | | | | |
| 36 | 33 | | | | | |
| 39 | 40 | | | | | |
| 42 | 53 | | | | | |
| 45 | 70 | | | | | |

This test shows that increased insecticidal results are obtained with compositions according to the invention containing liquid low-volatile diluent B of very different chemical formula when the physical characteristics of said diluents lie within the defined ranges.

TEST E

The following two compositions E-0 and E-1 were prepared and filled in aerosol containers (values expressed in percent by weight):

| | Component | E-0 | E-1 |
|---|---|---|---|
| Dioxacarb | A | 0,66 | 0,66 |
| T.U.O.B. (a) | B | — | 1.32 |
| Dichloromethane (b') | C | 27 | 27 |
| Ligroin (b) | D | 16 | 14,68 |
| Trichlorofluoromethane | E | 22 | 22 |
| Dichlorodifluoromethane | E | 33 | 33 |
| Diazinon (d') | F | 1,34 | 1,34 |

(d') 0,0-diethyl-0-(2-isopropyl-6-methyl-4-pyrimidinyl) thionophosphate employed as additional insecticidal active substance.

The content of each of these containers was sprayed on to one of the two faces of a glass plate the applied amount being 500 mg per plate. These plates were maintained at 15° C for 80 days, and the tests of insecticidal efficacy were then carried out on common cockroaches, as described in Test A. The obtained results are given in the following table.

| COMPOSITION | AGE (days) | TIME IN MINUTES 30 | 60 |
|---|---|---|---|
| E-0 | | 42 | 94 |
| E-1 | | 54 | 100 |
| E-0 | | 4 | 42 |
| E-1 | 45 | 44 | 92 |
| E-0 | | 6 | 64 |
| E-1 | 80 | 38 | 94 |

TEST E'

The procedure was repeated as in Test E except that, in this case, the glass plates were maintained at a temperature of 30° C. The recorded results were as follows:

| COMPOSITION | AGE (days) | TIME IN MINUTES 30 | 60 |
|---|---|---|---|
| E-0 | | 20 | 66 |
| E-1 | 10 | 58 | 100 |
| E-0 | | 14 | 36 |
| E-1 | 45 | 68 | 94 |
| E-0 | | 16 | 40 |
| E-1 | 80 | 34 | 100 |

Tests E and E' show that equally good results are obtained independently of the temperature at which the compositions according to the invention are evaporated.

TEST F

The following compositions F-0 to F-5 were prepared (percent by weight):

| | Component | F-0 | F-1 | F-2 | F-3 | F-4 | F-5 |
|---|---|---|---|---|---|---|---|
| Dioxacarb | A | 0.02 | 0.02 | 0.02 | 0.02 | 0.02 | 0.02 |
| T.U.O.B. (a) | B | — | 0.01 | 0.02 | 0.04 | 0.06 | 0.10 |
| Acetone (e) | C | | | Q.S.P. 100 | | | |

(e) liquid having a vapour pressure at 25° C equal to 225 Torr and a dissolving capacity for Dioxacarb of 28% at 20° C.

These compositions were tested on common cockroaches (Blattella orientalis), an amount of 2 microliters being deposited, by means of a microsyringe, on to the abdomen of each insect. For each composition, 24 insects were treated and then transferred after treatment to ventilated glass jars. The number of insects dead or in dorsal position was observed every hour; the ratio between the figures recorded every hour for composition E-0 and those for the other compositions was calculated, with the arbitrary value of 1 being given to the composition E-0.

| | F-0 | F-1 | F-2 | F-3 | F-4 | F-5 |
|---|---|---|---|---|---|---|
| 1 hour | 1 | 1,23 | 1,97 | 1,99 | 2,01 | 2,41 |
| 2 hours | 1 | 1,36 | 1,83 | 1,94 | 1,96 | 2,27 |
| 3 hours | 1 | 1,30 | 1,67 | 1,71 | 1,67 | 1,93 |
| 4 hours | 1 | 1,34 | 1,57 | 1,62 | 1,52 | 1,73 |
| 5 hours | 1 | 1,37 | 1,58 | 1,61 | 1,52 | 1,71 |
| 6 hours | 1 | 1,39 | 1,59 | 1,62 | 1,52 | 1,71 |
| 7 hours | 1 | 1,39 | 1,58 | 1,62 | 1,52 | 1,72 |
| Average | 1 | 1,34 | 1,68 | 1,73 | 1,67 | 1,92 |

This test is showing that satisfactory results are obtained with compositions according to the invention containing as few diluent B as 0.01% by weight of said compositions.

TEST G

The following three compositions G-0, G-1 and G-2 were prepared (percent by weight):

| | | Component | G-0 | G-1 | G-2 |
|---|---|---|---|---|---|
| Dioxacarb | | A | 0,2 | 0,2 | 0,2 |
| T.U.O.B. | (a) | B | — | 0,1 | 1,0 |
| Acetone | (e) | C | | Q. S. P. 100 | |

These solutions were applied in each case on to one of the two faces of 5 × 5 cm glass plates, the applied amount being 0.5 milliliter per plate. After evaporation of the acetone, which required several minutes, the plates were transferred individually to ventilated glass jars in each of which were about ten German cockroaches (Blattela germanica).

The cumulative proportions of insects dead or in dorsal position were recorded every 30 minutes for each composition; the obtained results were as follows:

| COMPOSITION | TIME IN MINUTES | | | |
|---|---|---|---|---|
| | 30 | 60 | 90 | 100 |
| G-0 | 7 | 17 | 30 | 37 |
| G-1 | 7 | 30 | 63 | 85 |
| G-2 | 18 | 77 | 100 | — | iplaneta americana), and the following results were recorded after storage of the plates for ten days:

| COMPOSITION | TIME IN MINUTES | | | |
|---|---|---|---|---|
| | 60 | 90 | 120 | 150 |
| H-0 | 6 | 7 | 9 | 11 |
| H-1 | 11 | 24 | 50 | 62 |
| H-2 | 9 | 20 | 49 | 61 |

TEST I

The following compositions I-0 to I-6 were prepared and filled in aerosol containers (values expressed in percent by weight):

| Component | | I-0 | I-1 | I-2 | I-3 | I-4 | I-5 | I-6 |
|---|---|---|---|---|---|---|---|---|
| A | Arprocarb (g) | 1 | 1 | 1 | 1 | 1 | 1 | 1 |
| B | Dioctyl phthalate (f) | — | — | 2 | — | — | — | — |
| B | Isopropyl myristate (c) (f') | — | 2 | — | — | — | — | — |
| B | Paraffin oil (f'') | — | — | — | — | — | — | 1 |
| B | Chlorohexadecane (c'') (f''') | — | — | — | 2 | — | 1 | — |
| B | Di(2-ethyl-hexyl) adipate (f'''') | — | — | — | — | 2 | — | — |
| B | T.U.O.B. (a) | — | — | — | — | — | 1 | 1 |
| C | Dichloromethane (b') (g') | 27,5 | 25,5 | 25,5 | 25,5 | 25,5 | 25,5 | 25,5 |
| D | Ligroin (b) (g'') | 16,5 | 16,5 | 16,5 | 16,5 | 16,5 | 16,5 | 16,5 |
| E | Trichlorofluoromethane | 22 | 22 | 22 | 22 | 22 | 22 | 22 |
| E | Dichlorodifluoromethane | 33 | 33 | 33 | 33 | 33 | 33 | 33 |

(f) dissolving capacity at 20° C equal to 2.6% Arprocarb;
(f') dissolving capacity at 20° C equal to 1.3% of Arprocarb;
(f'') semi-refined oil possessing a density equal to 0.867 at 15° C, a freezing point near to - 42° C, a vapour pressure of below 0.001 Torr, and a dissolving capacity at 20° C of practically nil with respect to the phenyl N-methyl-carbamates; the mixture 1:1 with 5-(3,6,9-trioxa-un-decyl-2-oxy)-1,3-benzodioxole has a dissolving capacity of 1.5% for Arprocarb at 20° C;
(f''') dissolving capacity for Arprocarb at 20° C equal to 0.4%; the (1:1) mixture with 5-(3,6,9-trioxa-un-decyl-2-oxy)-1,3-benzodioxole possesses a dissolving capacity at 20° C equal to 2% of Arprocarb;
(f'''') liquid possessing a vapour pressure at 25° C of approximately 0.007 Torr and a dissolving capacity of 2.8% of Arprocarb;
(g) common name designating 2-isopropoxy-phenyl N-methyl-carbamate;
(g') dissolving capacity at 20° C of approximately 48% of Arprocarb;
(g'') dissolving capacity at 20° C of approximately 0.2% of Arprocarb.

TEST H

The following three compositions H-0, H1 and H-2 were prepared (results expressed in percent by weight):

| | | Components | H-0 | H-1 | H-2 |
|---|---|---|---|---|---|
| Dioxacarb | | A | 0,02 | 0,02 | 0,02 |
| T.U.O.B. | (a) | B | — | 0,04 | — |
| Dibutyl phthalate | (a') | B | — | — | 0,04 |
| Acetone | (e) | C | Q. S. P. 100 | | |

Tests were carried out as in test G except that, in this case, the insects used were Madeira cockroaches (leucophaea maderas); the following results were obtained:

| COMPOSITION | TIME IN MINUTES | | | |
|---|---|---|---|---|
| | 60 | 90 | 120 | 150 |
| H-0 | 0 | 1 | 4 | 6 |
| H-1 | 0 | 4 | 17 | 39 |
| H-2 | 4 | 4 | 21 | 64 |

TEST H'

Tests were carried out as in test H except that, in this case, the insects used were American cockroaches (Per- The contents of each of the containers was sprayed on to one of the two faces of a glass plate, 20 × 10 cm in size, the amount applied being 600 mg per plate. After a standing time of 24 hours, tests to determine insecticidal efficacy were carried out on common cockroaches, these being placed on the treated face of the glass plate for one minute, and then transferred for observation to ventilated glass jars. The cumulative proportion of insects dead or in dorsal position was recorded every 3 minutes, the number of insects used for each composition being about 30. The proportions recorded are shown below.

| TIME IN MINUTES | I-0 | I-1 | I-2 | I-3 | I-4 | I-5 | I-6 |
|---|---|---|---|---|---|---|---|
| 3 | 3 | 18 | 10 | 13 | 23 | 18 | 13 |
| 6 | 7 | 48 | 78 | 65 | 40 | 33 | 63 |
| 9 | 70 | 98 | 100 | 93 | 95 | 95 | 95 |
| 12 | 90 | 100 | | 100 | 100 | 100 | 100 |

This test shows that in the compositions according to the invention Arprocarb behaves exactly as Dioxacarb.

TEST J

Three solutions were prepared having the following constituents (values expressed in per cent by weight):

|  | Component | 1 | 2 | 3 |
|---|---|---|---|---|
| Dioxacarb | A | 2,50 | 2,50 | 2,50 |
| Dibutyl phthalate (a') | B | 2,50 | 3,75 | 5,00 |
| Dichloromethane (b') | C | 95,00 | 93,75 | 92,50 |

These solutions were poured into a mixer containing talcum powder of a very high degree of fineness (amount retained less than 0.5% on 50 micron sieve); after mixing to obtain a good dispersion of solution and powder, the methylene chloride was evaporated off by means of a current of warm air (50° C). The proportions of talcum and solution were chosen to obtain the final powders J-1 to J-3 of the following compositions (values in per cent by weight):

|  | J-1 | J-2 | J-3 |
|---|---|---|---|
| Dioxacarb | 1,0 | 1,0 | 1,0 |
| Dibutyl phthalate | 1,0 | 1,5 | 2,0 |
| Talcum | 98,0 | 97,5 | 97,0 |

In addition, a standard formulation was prepared as follows by intimate mixing of the following constituents:

Dioxacarb : 1.0%
talcum : 99.0%

This mixture was placed into a needle mill to obtain a powder giving an oversize amount of less than 0.05% on a 50 micron sieve. The designation given to this powder was J-0.

Insecticidal efficacy tests were carried out on two species of cockroaches in the case of each of the four powders thus prepared, under the following conditions. An amount of 0.45 mg of powder was deposited into a Petri dish of 17 cm diameter by means of a pneumatic device enabling a fine and uniform layer of powder to be obtained. Ten insects were then placed into the dish, and an observation made every 15 minutes of the number of insects dead or in dorsal position. In the case of each species of insect, ten boxes each containing ten insects were used. The summarised results are shown in the following table.

| Time in minutes | Periplanate amaricana | | | | Blattella germanica | | | |
|---|---|---|---|---|---|---|---|---|
|  | J-0 | J-1 | J-2 | J-3 | J-0 | J-1 | J-2 | J-3 |
| 60 | 2 | 16 | 8 | 6 | 10 | 32 | 16 | 10 |
| 75 | 12 | 46 | 36 | 14 | 11 | 42 | 18 | 18 |
| 90 | 30 | 70 | 92 | 76 | 12 | 56 | 28 | 24 |
| 105 | 36 | 82 | 98 | 88 | 12 | 60 | 36 | 28 |
| 120 | 46 | 90 | 100 | 94 | 12 | 62 | 42 | 30 |

TEST K

The following two compositions K-0 and K-1 were prepared in an aerosol container:

| Component |  | K-0 | K-1 |
|---|---|---|---|
| A | Dioxacarb | 0,5 | 0,5 |
| B | Dibutyl phthalate (a') | — | 1,0 |
| C | Dichloromethane (b') | 17,9 | 16,9 |
| C | Tetrahydrofuran (d) | 1,6 | 1,6 |
| E | Trichlorofluoromethane | 40,0 | 40,0 |
| E | Dichlorodifluoromethane | 40,0 | 40,0 |

These tests were carried out on five-day old house flies freely flying about in a room of 27 cubic meters. In the case of each test, an amount of 4 grams of the composition being tested was vaporised in the atmosphere of the room, and every three minutes account was taken of the number of fallen insects. The operation was performed six times for each composition. The recorded results are given below as average percentages (KD%) of fallen flies at each count.

| Time in minutes | K-0 | K-1 |
|---|---|---|
| 12 | 1,7 | 9,8 |
| 15 | 6,7 | 26,0 |
| 18 | 14,3 | 42,7 |
| 21 | 24,9 | 52,1 |
| 24 | 36,8 | 62,0 |
| 27 | 46,4 | 68,7 |
| 30 | 54,9 | 74,0 |

TEST L

A solution was prepared having the following composition (values expressed in per cent by weight):
(A) Dioxacarb: 6.25
(B) T.U.O.B. (a): 6.25
(C) Chloroform (e): 87.50
e. Liquid having a vapour pressure at 25° C equal to 194 Torr and a dissolving capacity of 34% of Dioxacarb at 20° C.

This solution was poured into a mixer containing talcum powder of a very high degree of fineness (a small amount of about 0.5%, retained on a 50 micron sieve); after mixing to obtain a good distribution of the solution on the powder, the chloroform was evaporated off by means of a current of warm air (50° C); a powder was obtained in this manner and designated as L-3.

In addition two further formulations L-1 and L-2 were prepared by intimate mixing of the constituents without the aid of any solvent; these mixtures were ground in a needle grinder to obtain powders giving an oversize residue on a 50 micron sieve, amounting to less than 0.05%.

The table below shows the composition of the three prepared powders (values expressed in per cent by weight):

|  | L-1 | L-2 | L-3 |
|---|---|---|---|
| Dioxacarb | 2,5 | 2,5 | 2,5 |
| T.U.O.B. (a) | — | 2,5 | 2,5 |
| Talcum | 97,5 | 95,0 | 95,0 |

Insecticidal effectiveness tests were carried out on aphids (Aphis Fabae) with each of the above three powders, the test conditions being as follows:

Fifteen-day old young broad bean plants were used, these having an average of eight leaves and being infested by natural means by aphids (ca. 260 insects on average per plant). These plants were divided into three lots of ten plants each, and each lot was treated by the sprinkling on of one of the three powders in an amount of five milligrams of powder per plant. At the end of six hours a count was taken of the number of surviving insects on each lot of plants. The results recorded are shown in the table below:

| Powders used for the treatment of the plant lot | Number of surviving aphids per lot |
|---|---|
| L-1 | 1 540 |
| L-2 | 1 240 |
| L-3 | 132 |

These results show the clear superiority of the formulation L-3 prepared according to the invention; it is seen that a powder having the same constituents A and B (L-2), but prepared without the aid of a volatile liquid C, is not appreciably superior to a powder (L-1) not containing constituent B.

TEST M

Three powders were prepared in the manner described in test L. These powders were designated as M-1, M-2 and M-3, corresponding respectively to the powders L-1, L-2 and L-3. They were tested on Phormia terranovae flies under the following conditions. By means of a pneumatic device enabling a fine and uniform layer to be obtained, an amount of 0.45 mg of powder was deposited in a Petri dish 17 cm in diameter and 20 mm in height. Twenty insects were then introduced, and a count taken every 15 minutes of the insects dead or in dorsal position. For each powder there were used five boxes of twenty insects each. The summarised results are shown below.

| Minutes | M-1 | M-2 | M-3 |
|---|---|---|---|
| 60 | 30 | 12 | 52 |
| 75 | 36 | 16 | 78 |
| 90 | 44 | 18 | 86 |
| 105 | 44 | 20 | 90 |
| 120 | 58 | 22 | 92 |
| 135 | 54 | 26 | 94 |
| 150 | 56 | 30 | 98 |

It is seen here too that the powder M-3, prepared according to the invention, is clearly superior to the two others; there is observed no effect of potentialisation of the liquid B (T.U.O.B.) in the case of the powder M-2, which appears even inferior to the powder M-1.

Tests J to M show that equally good insecticidal results are obtained with the compositions according to the invention when these latter are deposited on a pulverulent carrier and evaporated therefrom.

The preceding test illustrate the efficacy of the compositions according to the invention; in all cases, the effectiveness of the active substance is clearly improved when the solution containing it also contains a heavy diluent in which the active substance is difficultly soluble, such as dibutyl phthalate, dioctyl phthalate, di(-2-ethyl-hexyl)-adipate, isopropyl myristate, chlorohexadecane, tetrachloro-diphenyl and 5-(3,6,9-trioxa-2-oxy-undecyl)-1,3-benzodioxole, or the mixtures of the last-mentioned with a paraffin oil, or chlorohexadecane and a volatile solvent readily dissolving the carbamic ester, such as acetone, dichloromethane and/or tetrahydrofuran.

The tests described in the foregoing were carried out on various species of orthoptera, diptera and hemiptera; the compositions according to the invention are, of course equally suitable for the destruction of other species of orthoptera such as, for example, grasshoppers (locusts), diptera such as, for example, Stomoxynae, culex, aedes, and hemiptera such as, for example, cimex and Triatomidae, as well as other orders of insects such as, for example, coleoptera (*Orynophilus surinamensis, Dermestes Frischii, Trogodoram granarium, Attagenus pellio, Tribolium confusum, Guathocerus cornutus, Tenebrio molitor, Sitophilus granarius, Leptinotarsa decemlineata*), hemiptera (*Aphidae, Rhodnius prolixus*, hymenoptera (*Formicidae*) and lepidoptera (*Sitotroga cerealila, Plodia interpunotella*).

The following compositions are given as further examples of the invention (values expressed in per cent by weight).

EXAMPLES 1 to 12
Compositions for aerosols (liquids under pressure)

| | | 1 | 2 | 3 | 4 | 5 | 6 | 7 | 8 | 9 | 10 | 11 | 12 |
|---|---|---|---|---|---|---|---|---|---|---|---|---|---|
| A | Dioxacrab | 2 | 2 | 0,5 | — | — | 2 | 1 | — | 1,5 | 1,5 | — | — |
| | Arprocarb (g) | — | — | — | 2 | — | 1 | — | 1 | — | — | 1,5 | — |
| | MCPOP (h) | — | — | — | — | 2 | — | — | — | — | — | — | 1 |
| B | T.U.O.B. (a) | 4 | — | — | — | — | — | — | 1 | — | 1,5 | — | — |
| | Dibutyl phthalate | — | 4 | — | — | — | 1 | 2 | — | — | — | — | — |
| | Dioctyl phthalate | — | — | — | 4 | 1 | — | — | — | — | — | — | — |
| | Isopropyl myristate | — | — | 0,5 | — | — | — | 1 | 1 | — | 3 | — | — |
| | Chloro-1-hexadecane | — | — | — | — | 1 | 3 | — | 1 | — | — | 4 | 5 |
| | Paraffin oil | — | — | — | — | — | — | — | — | 5 | — | 4 | 5 |
| C | Dichloromethane | 25,5 | 25,5 | 43 | 28,5 | 41,7 | 37,4 | 36 | 36 | 33 | 39 | 26,5 | 38,5 |
| | Tetrahydrofuran (d) (j) | 2 | 2 | — | 5,5 | — | 5 | — | — | — | — | 2 | — |
| | Acetonitrile (j') | — | — | — | — | — | — | — | — | 2 | — | — | — |
| | Methanol (j'') | — | — | 4 | — | — | — | — | — | — | — | — | — |
| | Dioxane (j''') | — | — | — | — | — | — | — | — | — | 2 | — | — |
| D | Amyl alcohol (k) | 0,5 | — | — | — | — | — | — | — | — | — | — | — |
| | Isopropanol (k') | — | 0,5 | — | — | — | — | — | — | — | — | — | — |
| | Ligroin (b) (g'') | 11 | 11 | — | 10 | — | — | — | — | 8 | — | 6 | — |
| E | Butane | — | — | — | — | — | — | 30 | 30 | — | — | — | 50 |
| | Dichlorodifluoromethane | 33 | 33 | 26 | 30 | 27 | 25 | 15 | 15 | 30 | 26 | 33 | — |
| | Trichlorofluoromethane | 22 | 22 | 26 | 20 | 27 | 25 | 15 | 15 | 20 | 26 | 22 | — |
| F | Lindane (l) | — | — | — | — | — | — | — | — | — | — | — | 0,5 |
| | Diazinon (d') | — | — | — | — | — | — | — | — | — | 1 | 1 | — |
| | Diclorvos (l') | — | — | — | — | — | — | — | — | 0,5 | — | — | — |
| G | Lavender oil | — | — | — | — | 0,3 | — | — | — | — | — | — | — |

-continued

EXAMPLES 1 to 12
Compositions for aerosols (liquids under pressure)

| | 1 | 2 | 3 | 4 | 5 | 6 | 7 | 8 | 9 | 10 | 11 | 12 |
|---|---|---|---|---|---|---|---|---|---|---|---|---|
| pine oil | — | — | — | — | — | 0,6 | — | — | — | — | — | — |

(h) Abbreviation for 2-propargyloxy-phenyl N-methyl-carbamate.
(j) Dissolving capacity at 20° C approximately 50% of Arprocarb.
(j') Liquid possessing a vapour pressure at 25° C equal to 86 Torr, and a dissolving capacity at 20° C of 35.5% for Dioxacarb.
(j'') Liquid having a vapour pressure at 25° C equal to 127 Torr, and a dissolving capacity at 20° C of 20.5% for Dioxacarb.
(j''') Liquid having a vapour pressure at 25° C equal to 35 Torr, and a dissolving capacity at 20° C of 23% for Dioxacarb.
(k) Liquid having a vapour pressure at 25° C equal to 2.5 Torr, and a dissolving capacity at 20° C of 2.6% for Dioxacarb.
(k') Liquid having a vapour pressure at 25° C dissolving to 44 Torr, and a disslving capacity at 20° C of 4.5% for Dioxacarb.
(l) Common name for the gamma isomer of 1,2,3,4,5,6-hexachloro-cyclohexane.
(l') Common name for 0-(2,2-dichloro-vinyl)-0,0-dimethyl phosphate, known also under the name of DDVP.

EXAMPLES 13 to 25
Liquid compositions without pressure

| | | 13 | 14 | 15 | 16 | 17 | 18 | 19 | 20 | 21 | 22 | 23 | 24 | 25 |
|---|---|---|---|---|---|---|---|---|---|---|---|---|---|---|
| A | Dioxacarb | 2 | 3 | 4 | 5 | — | 1,5 | 8 | — | — | — | — | — | 2 |
| | Arprocarb (g) | — | — | — | — | 3 | — | — | — | — | — | — | — | — |
| | MCDMP (m) | — | — | — | — | — | 1,5 | — | 3 | — | — | — | — | — |
| | MCMDP (m') | — | — | — | — | — | — | — | — | 2 | 4 | — | — | — |
| | MCDP (m'') | — | — | — | — | — | — | 2 | — | — | — | 2 | 4 | — |
| B | T.U.O.B. (a) | — | 2 | — | 2 | — | — | — | — | — | — | — | — | — |
| | Dibutyl phthalate | 4 | — | — | 3 | — | — | — | — | — | — | — | — | 4 |
| | Isopropyl myristate | — | — | — | — | — | 8 | 5 | 5 | — | — | — | 6 | — |
| | Chlorohexadecane | — | 4 | — | — | — | — | 5 | — | 5 | — | 3 | — | — |
| | Bis (2-ethyl-hexyl) adipate | — | — | 5 | — | 7 | — | — | — | — | — | — | — | — |
| | Tetrachlorodiphenyl | — | — | 5 | — | — | — | — | — | — | 6 | — | — | — |
| C | Nitromethane (n) | — | 10 | — | — | — | — | — | — | — | — | — | — | — |
| | Dichloromethane | — | — | — | — | — | — | — | — | — | — | — | — | 20 |
| | Methyl acetate (n') | 9 | — | 30 | 50 | 30 | — | — | — | 92 | 45 | 24 | — | — |
| | Ethyl acetate (p) | — | 15 | — | — | — | 25 | 50 | — | — | — | — | 75 | — |
| | Methanol | 30 | 25 | — | — | — | — | — | 92 | — | 45 | 20 | — | — |
| | Tetrahydrofuran | 15 | — | — | 10 | 30 | 15 | 40 | — | — | — | 10 | 15 | — |
| | 2-Methoxy-ethanol (p') | — | — | 20 | 10 | — | 10 | — | — | — | — | 10 | — | — |
| D | Benzene (q) | — | 20 | 29,5 | — | — | — | — | — | — | — | — | — | — |
| | Butyl chloride (q') | — | — | — | 20 | — | 19 | — | — | — | — | — | — | — |
| | Heptane (q'') | 40 | 20 | — | — | 29 | 19 | — | — | — | — | 30 | — | — |
| | Stearone | — | 1 | — | — | — | 1 | — | — | — | — | — | — | — |
| | "Isopar G" (x') | — | — | — | — | — | — | — | — | — | — | — | — | 20 |
| | Colophony ester (q''') | — | — | 4 | — | — | — | — | — | — | — | — | — | — |
| | 1,1,1-Trichloro ethane (x) | — | — | — | — | — | — | — | — | — | — | — | — | 54 |
| F | Fenthion (r) | — | — | — | — | — | — | — | — | — | — | 1 | — | — |
| | MCMQ (r') | — | — | — | — | — | — | — | — | 1 | — | — | — | — |
| | Chlordane (r'') | — | — | 2 | — | — | — | — | — | — | — | — | — | — |
| | Carbaryl (r''') | — | — | — | — | 1 | — | — | — | — | — | — | — | — |
| G | Yellow dyestuff (s) | — | — | 0,5 | — | — | — | 1 | — | — | — | — | — | — |

(m) Abbreviation for dimethoxy-2-methyl-phenyl N-methyl carbamate.
(m') Abbreviation for 2-(4-methyl-1,3-dioxolan-2-yl)-phenyl N-methyl carbamate.
(m'') Abbreviation for 2-(1,3-dioxan-2-yl)-phenyl N-methyl carbamate.
(n) Liquid having a vapour pressure at 25° C equal to 34 Torr, and a dissolving capacity for Dioxacarb of 27.5% at 20° C.
(n') Liquid having a vapour pressure at 25° C equal to 216 Torr, and a dissolving capacity at 20° C of 19.6% of Dioxacarb and 41% for Arprocarb.
(p) Liquid having a vapour pressure at 25° C equal to 97 Torr, and a dissolving capacity at 20° C of 10.5% for Dioxacarb.
(p') Liquid having a vapour pressure at 25° C equal to 8.6 Torr, and a dissolving capacity at 20° C of about 15% for Dioxacarb.
(q) Liquid having a vapour pressure at 25° C equal to 95 Torr, and a dissolving capacity at 20° C of 3% for Dioxacarb.
(q') Liquid having a vapour pressure at 25° C equal to 102 Torr, and a dissolving capacity at 20° C of 2% for Dioxacarb.
(q'') Liquid having a vapour pressure at 25° C equal to 38.5 Torr, and a dissolving capacity at 20° C of about 0.2% for Dioxacarb and 0.3% for Arprocarb.
(q''') Hard resin having a softening point of about 100° C and an acid number of approximatey 160.
(r) Common name designating O,O-dimethyl O-3-methyl-4-methylthio-phenyl thionophosphate.
(r') Abbreviation for 2-methyl-8-quinolyl N-methyl-carbamate.
(r'') Common name designating 1,2,4,5,6,7,8,8-octa-chloro-3a,4,7,7a-tetrahydro-4,7-methano-indane.
(r''') Common name designating alphanaphthyl-N-methyl carbamate.
(s) 5-Hydroxy-3-methyl-1-phenyl-4-phenylazo-pyrazole (Colour Index No. 12.700 - Solvent Yellow 16).

EXAMPLES 26 to 37
Solid preparations obtained from liquid compositions

| | 26 | 27 | 28 | 29 | 30 | 31 | 32 | 33 | 34 | 35 | 36 | 37 |
|---|---|---|---|---|---|---|---|---|---|---|---|---|
| Kaolin | | | | | | EMPLOYED CARRIER | | | | | | |
| Kaolin | 100 | 80 | — | — | 100 | — | — | 20 | — | — | — | — |
| Dried clay | — | — | — | — | — | 70 | — | — | — | — | — | — |
| Aluminium silicate | — | 20 | — | — | — | 30 | — | — | — | — | — | — |
| Soya bean flour | — | — | — | 40 | — | — | — | 40 | 40 | — | — | — |
| Sugar | — | — | — | 40 | — | — | — | 40 | 60 | 100 | — | — |
| Granulated marble | — | — | — | — | — | — | — | — | — | — | 100 | 100 |

-continued

EXAMPLES 26 to 37
Solid preparations obtained from liquid compositions

| | | 26 | 27 | 28 | 29 | 30 | 31 | 32 | 33 | 34 | 35 | 36 | 37 |
|---|---|---|---|---|---|---|---|---|---|---|---|---|---|
| | Cellulose board | — | — | 100 | — | — | — | 100 | — | — | — | — | — |
| | Parts by weight of carrier | 97,1 | 95 | 94 | 96 | 94,3 | 94 | 96,5 | 95 | 95 | 94,9 | 97 | 96 |

EMPLOYED LIQUID COMPOSITION

| | | 26 | 27 | 28 | 29 | 30 | 31 | 32 | 33 | 34 | 35 | 36 | 37 |
|---|---|---|---|---|---|---|---|---|---|---|---|---|---|
| A | Dioxacarb | 10 | 10 | 10 | — | — | 5 | 6 | 5 | 6 | — | 10 | 10 |
| | Arprocarb (g) | — | — | — | 10 | 10 | 5 | 4 | — | — | — | — | — |
| | MCMDP (m') | — | — | — | — | — | — | — | 5 | 4 | 10 | — | — |
| B | T.U.O.B. (a) | 24 | 20 | — | 10 | — | 5 | — | — | 44 | — | — | 10 |
| | Dibutyl phthalate | — | 20 | 20 | — | — | — | — | 2,5 | — | — | 10 | — |
| | Dioctyl phthalate | 24 | — | — | — | 20 | — | 2 | — | — | 6 | — | — |
| | Chlorohexadecane | — | — | — | 20 | — | — | 2 | — | — | — | — | 10 |
| | Paraffin oil | — | — | — | — | — | 5 | — | — | — | 6 | — | — |
| | Tetrachlorodiphenyl | — | — | — | — | — | 5 | — | 7,5 | — | — | — | — |
| C | Dichloromethane | 42 | 50 | 30 | 40 | — | — | — | 42 | — | — | 40 | 60 |
| | Acetone | — | — | — | — | 25 | — | — | 40 | 40 | — | — | — |
| | Methanol | — | — | — | — | — | — | — | — | — | 68 | — | — |
| | Ethanol (t) | — | — | 10 | — | — | 70 | — | — | — | — | — | — |
| | Isopropanol (k') (t') | — | — | — | — | 20 | — | — | — | — | — | — | — |
| | Methyl acetate | — | — | — | — | — | — | 86 | — | 40 | — | — | — |
| D | Benzene | — | — | — | — | — | — | — | — | — | — | 20 | — |
| | Hexane (u) | — | — | 20 | — | — | — | — | — | — | — | — | — |
| | Pentane (u') | — | — | — | 20 | 17 | — | — | — | — | — | — | — |
| | Trichlorethylene (u") | — | — | — | — | — | — | — | — | — | — | 20 | — |
| | Carnauba wax | — | — | — | — | — | — | — | — | 6 | — | — | — |
| | Polyvinyl acetate (u''') | — | — | — | — | — | — | — | — | — | 6 | — | — |
| | Paraffin 60/62° | — | — | — | — | — | 5 | — | — | — | — | — | — |
| | Trichloro-1,1,1-ethane (x) | — | — | — | — | — | — | — | — | — | — | — | — |
| F | Dieldrine (v) | — | — | — | — | 8 | — | — | — | — | — | — | — |
| | Fenchlorphos (v') | — | — | — | — | — | — | — | — | — | — | — | 10 |
| | Dimetilan (v") | — | — | — | — | — | — | — | — | — | 4 | — | — |
| G | Red dyestuff (w) | — | — | — | — | — | — | — | 1 | — | 2 | — | — |
| | Parts by weight of liquid | 5 | 10 | 20 | 10 | 15 | 20 | 25 | 20 | 25 | 15 | 15 | 10 |

(t) Liquid having a vapour pressure at 25° C equal to 59 Torr, and a dissolving capacity at 20° C of 8% of dioxacarb and 40% of Aprocarb.
(t') Dissolving capacity at 20° C approximately 30% of Arprocarb.
(u) Liquid having a vapour pressure at 25° C equal to 151 Torr, and a dissolving capacity at 20° C of approximately 0.2% of Dioxacarb and 0.3% of Arprocarb.
(u') Liquid having a vapour pressure at 25° C equal to 513 Torr, and a dissolving capacity at 20° C of approximately 0.2% for Dioxacarb and 0.3% for Arprocarb.
(u") Liquid having a vapour pressure at 25° C equal to 74 Torr, and a dissolving capacity at 20° C of approximately 2% for Dioxacarb.
(u''') Polyvinyl acetate of low viscosity (10 cp with 20 g in 100 g of the mixture ethanol/ethyl acetate 65:15 at 20° C).
(v) Common name designating endo-oxo-1,2,3,4,10,10-hexachloro-6,7-epoxy-1,4,4a,5,6,7,8,8a-octahydro-1,4,5,8-dimethano-naphthalene.
(v') Common name designating 0,0-dimethyl-2,4,5-0-trichloro-phenyl thionophosphate.
(v") Common name designating 1-dimethylcarbamoyl-5-methyl-pyrazolyl-3 N,N-dimethyl carbamate.
(w) 1-(4-Phenylazo-phenylazo)-2-ethylamino-naphthalene (Colour Index No. 26.050 - Solvent Red 19).
(x) Liquid having a vapour pressure at 25° C equal to 121 Torr, and a dissolving capacity at 20° C of 2.3% for Dioxacarb.
(x') Distillation range between 159 and 177° C of branched aliphatic hydrocarbons obtained by synthesis, marketed by the firm Societe Esso Standard, containing a mixture of octanes, nonanes and decanes, possessing at 25° C a vapour pressure of between 15 and 20 Torr, and having a dissolving capacity at 20° C of below 0.1% for Dioxacarb.

PRODUCT OBTAINED AFTER EVAPORATION OF THE VOLATILE LIQUIDS

| | 26 | 27 | 28 | 29 | 30 | 31 | 32 | 33 | 34 | 35 | 36 | 37 |
|---|---|---|---|---|---|---|---|---|---|---|---|---|
| Dioxacarb | 0,5 | 1 | 2 | — | — | 1 | 1,5 | 1 | 1,5 | — | 1,5 | 1 |
| Arprocarb (g) | — | — | — | 1 | 1,5 | 1 | 1 | — | — | — | — | — |
| MCMDP (m') | — | — | — | — | — | — | — | 1 | 1 | 1,5 | — | — |
| T.U.O.B. (a) | 1,2 | 2 | — | 1 | — | 1 | — | — | 1 | — | — | 1 |
| Dibutyl phthalate | — | 2 | 4 | — | — | — | — | 0,5 | — | — | 1,5 | — |
| Dioctyl phthalate | 1,2 | — | — | — | 3 | — | 0,5 | — | — | 0,9 | — | — |
| Chlorohexadecane | — | — | — | 2 | — | — | 0,5 | — | — | — | — | 1 |
| Paraffin oil | — | — | — | — | — | 1 | — | — | — | 0,9 | — | — |
| Tetrachlorodiphenyl | — | — | — | — | — | 1 | — | 1,5 | — | — | — | — |
| Carnauba wax | — | — | — | — | — | — | — | — | 1,5 | — | — | — |
| Polyvinyl acetate (u''') | — | — | — | — | — | — | — | — | — | 0,9 | — | — |
| Paraffin 60/62° | — | — | — | — | — | 1 | — | — | — | — | — | — |
| Dieldrine (v) | — | — | — | — | 1,2 | — | — | — | — | — | — | — |
| Fenchlorphos (v') | — | — | — | — | — | — | — | — | — | — | — | 1 |
| Dimetilan (v") | — | — | — | — | — | — | — | — | — | 0,6 | — | — |
| Red dyestuff (w) | — | — | — | — | — | — | 0,2 | — | 0,3 | — | — | — |
| Kaolin | 97,1 | 76 | — | — | 94,3 | — | — | 19 | — | — | — | — |
| Dried clay | — | — | — | — | — | 65,8 | — | — | — | — | — | — |
| Aluminium silicate | — | 19 | — | — | — | 28,2 | — | — | — | — | — | — |
| Soya bean flour | — | — | — | 48 | — | — | 38 | 38 | — | — | — | — |
| Sugar | — | — | — | 48 | — | — | 38 | 57 | — | — | — | — |
| Granulated marble | — | — | — | — | — | — | — | — | — | — | — | — |

| -continued |
| --- |
| PRODUCT OBTAINED AFTER EVAPORATION OF THE VOLATILE LIQUIDS |

| | 26 | 27 | 28 | 29 | 30 | 31 | 32 | 33 | 34 | 35 | 36 | 37 |
| --- | --- | --- | --- | --- | --- | --- | --- | --- | --- | --- | --- | --- |
| Cellulose board | — | — | 94 | — | — | — | 96,5 | — | — | 94,9 | 97 | 96 |

(t) Liquid having a vapour pressure at 25° C equal to 59 Torr, and a dissolving capacity at 20° C of 8% of dioxacarb and 40% of Arprocarb.
(t') Disslving capacity at 20° C approximately 30% of Arprocarb.
(u) Liquid having a vapour pressure at 25° C equal to 151 Torr, and a dissolving capacity at 20° C of approximately 0.2% of Dioxacarb and 0.3% of Arprocarb.
(u') Liquid having a vapour pressure at 25° C equal to 513 Torr, and a dissolving capacity at 20° C of approximately 0.2% for Dioxacarb and 0.3% for Arprocarb.
(u'') Liquid having a vapour pressure at 25° C equal to 74 Torr, and a dissolving capacity at 20° C of approximately 2% for Dioxacarb.
(u''') Polyvinyl acetate of low viscosity (10 cp with 20 g in 100 g of the mixture ethanol/ethyl acetate 65:15 at 20° C).
(v) Common name designating endo-oxo-1,2,3,4,10,10-hexachloro-6,7-epoxy-1,4,4a,5,6,7,8,8a-octahydro-1,4,5,8-dimethano-naphthalene.
(v') Common name designating O,O-dimethyl-2,4,5-O-trichloro-phenyl thionophosphate.
(v'') Common name designating 1-dimethylcarbamoyl-5-methyl-pyrazolyl-3 N,N-dimethyl carbamate.
(w) 1-(4-Phenylazo-phenylazo)-2-ethylamino-naphthalene (Colour Index No. 26.050 - Solvent Red 19).
(z) Liquid having a vapour pressure at 25° C equal to 121 Torr, and a dissolving capacity at 20° C of 2.3% for Dioxacarb.
(x') Distillation range between 159 and 177° C of branched aliphatic hydrocarbons obtained by synthesis, marketed by the firm SocitèEsso Standard, containing a mixture of octanes, nonanes and decanes, possessing at 25° C a vapour pressure of between 15 and 20 Torr, and having a dissolving capacity at 20° C of below 0.1% for Dioxacarb.

We claim:
1. An insecticidal composition in the form of a liquid organic homogeneous solution comprising as essential components (A) from about 0.01 to 10%, based on the weight of the composition, of an ortho-substituted phenyl N-methyl-carbamate of the following formula:

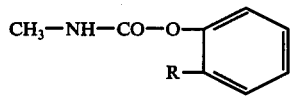

wherein R is an unsubstituted 1,3-dioxolan-2-yl radical or substituted by one or two methyl groups; and as sole solvent carrier for said component (A) a homogeneous mixture essentially consisting of
B. from about 0.01 to 10%, based on the weight of the composition of an organic diluent which is selected from the group consisting of vaseline oil, paraffin oil, hexadecane, 1-chlorohexadecane, 1-bromotetradecane, tetrachlorodiphenyl, isopropylmyristate, di(2-ethylhexyl) adipate, dibutylphthalate, dioctylphthalate, 5-(3,6,9-trioxa-undecyl-2-oxy)-1,3-benzodioxole, glycerol, 5,8,11-trioxapentadecane, 2-amino-2-ethyl-1,3-propanediol, ter.dodecane-thiol, oleone, octanoic acid, oleic acid, 2-dodecyl-succinic acid anhydride, olive oil, line oil and mixtures thereof, the weight proportion between component B and component A ranging between 0.2 and 10, with component B having a maximum dissolving capacity for component A of 5%, by weight, at 20° C. and
C. from about 25 to 99%, based on the weight of the composition, of an organic solvent, which is selected from the group consisting of dichloromethane, trichloromethane, methylacetate, ethylacetate, propylacetate, isopropylacetate, butylacetate, isobutylacetate, sec. butylacetate, methylpropionate, ethylpropionate, methylbutyrate, ethylbutyrate, 2-methoxyethyl acetate, tetrahydrofuran, dioxan, 2-methoxy-ethanol, methanol, ethanol, isopropanol, acetone, methyl-ethyl-ketone, nitromethane and acetonitrile, with component C having a dissolving capacity for component A of at least 5%, by weight, at 20° C. and
D. from 0 to about 75%, based on the weight of the composition of an organic diluent which is selected from the group consisting of pentane, hexane, heptane, 1-chlorobutane, 1,1,1-trichloroethane, trichloroethylene, benzene, isopropanol, amyl alcohol and light petroleum fractions having a distillation range between about 70° and 250° C. and which are soluble in A + B + C liquid at 25° C, have a vapour pressure at 25° C between 0.01 and 150 Torr and are able to dissolve at 20° C between 0 and 5%, by weight, of component A.

2. The composition according to claim 5, wherein component B is selected from the group consisting of vaseline oil, paraffin oil, hexadecane, 1-chlorohexadecane, 1-bromotetradecane, tetrachlorodiphenyl, isopropylmyristate, dibutylphthalate, dioctylphthalate and 5-(3,6,9-trioxaundecyl-2-oxy)-1,3-benzodioxole, component C is selected from the group consisting of dichloromethane, trichloromethane, tetrahydrofuran and acetone and component D, when it is present, is selected from the group consisting of petroleum fractions of branched aliphatic hydrocarbons having a distillation range between about 90° and 210° C.

3. The composition as described in claim 1, wherein component D has a vapour pressure of from about 10 Torr to 100 Torr at 25° C.

4. The composition as described in claim 1, wherein said composition contains a liquefied gas soluble in the whole formed by A + B + C, and usable as aerosol propellant.

5. The composition as described in claim 1, wherein said additional insecticidally active agent which also contains an insecticidally effective amount of 0,0-diethyl 0-(2-isopropyl-6-methyl-4-pyrimidinyl) thionophosphate.

6. The composition according to claim 1, essentially consisting of:
 about 2% of 2-(1,3-dioxolan-2-yl)-phenyl N-methyl-carbamate,
 about 4% of dibutylphthalate,
 about 25.5% of dichloromethane,
 about 2% of tetrahydrofuran,
 about 0.5% of isopropanol or of tert.butanol,
 about 11% of a light fraction of petroleum or of heptane
 about 33% of dichlorodifluoromethane and
 about 22% of trichlorofluoromethane,
all proportions being weight proportions based on the total weight of said composition.

7. The composition according to claim 1, essentially consisting of:

about 2% of 2-(1,3-dioxolan-2-yl)-phenyl N-methyl-carbamate,
about 4% of dibutylphthalate,
about 20% of dichloromethane,
about 20% of a light fraction of petroleum and about 54% trichloroethane,
all proportions being weight proportions based on the total weight of said composition.

* * * * *